United States Patent [19]

Childers

[11] Patent Number: 5,173,258
[45] Date of Patent: Dec. 22, 1992

[54] RECIRCULATION, VAPOR AND HUMIDITY CONTROL IN A SEALABLE ENCLOSURE

[75] Inventor: Robert W. Childers, Erie, Pa.

[73] Assignee: American Sterilizer Company, Erie, Pa.

[21] Appl. No.: 419,993

[22] Filed: Oct. 11, 1989

[51] Int. Cl.$^5$ .................................................. A61L 2/20
[52] U.S. Cl. ..................................... 422/27; 422/30; 422/292; 422/294; 422/307; 392/399
[58] Field of Search ............... 422/292, 294, 299, 302, 422/307, 29, 27, 30, 174, 177, 900, 905; 219/271, 430, 439

[56] References Cited

U.S. PATENT DOCUMENTS

| | | | |
|---|---|---|---|
| 3,443,884 | 5/1969 | Linder | 422/298 |
| 3,620,265 | 11/1971 | Strople et al. | 422/28 X |
| 3,687,612 | 8/1972 | Ernst | 422/28 X |
| 4,230,571 | 10/1980 | Dadd | 422/29 |
| 4,435,194 | 3/1984 | Picard et al. | 422/29 X |
| 4,909,999 | 3/1990 | Cummings et al. | 422/298 |

FOREIGN PATENT DOCUMENTS 2745961 10/1977 Fed. Rep. of Germany .
3523310 6/1985 Fed. Rep. of Germany .

OTHER PUBLICATIONS

*Disinfection, Sterilization and Preservation*, S. S. Block, 3rd ed., Lea & Febiger, 1983, Philadelphia, Pa., pp. 877-881.

Decontamination, Sterilization, Disinfection, Sanitization—The Concepts—The Facts, American Sterilizer Co., Erie, Pa., pp. 1-18.

*Primary Examiner*—Lynn M. Kummert
*Assistant Examiner*—Amalia L. Santiago
*Attorney, Agent, or Firm*—Kirkpatrick & Lockhart

[57] ABSTRACT

A recirculation/drying unit is provided for connection to a sealable enclosure. The unit and the enclosure form a closed circuit through which the gaseous medium of the enclosure is circulated, filtered, dehumidified or optionally, humidified, and returned to the enclosure. A vapor decontaminant is carried into and through the enclosure by the gaseous medium for a predetermined period of time sufficient to sterilize, disinfect or sanitize the gaseous medium, the enclosure and its contents. The decontaminant is returned to the unit for conversion into a form suitable for release into the atmosphere. The unit preferably includes filters, an air pump, a drier, a reservoir of liquid decontaminant, a reservoir of water, an injection pump, at least one vaporizer and at least one converter.

18 Claims, 4 Drawing Sheets (F/V=.0151, H.L.=5, R.H.=5, C=8.4:4.5 mg/liter)

(F/V=.0151, H.L.=10, R.H.=5, C=8.4:4.5 mg/liter)

RECIRCULATION, VAPOR AND HUMIDITY CONTROL IN A SEALABLE ENCLOSURE

BACKGROUND OF THE INVENTION

1. Field of the Invention

The present invention relates to sterilization systems, and more particularly, to a circuit for recirculating, filtering and controlling the vapor content of the gaseous medium in a sealable enclosure.

2. Description of the Prior Art

Conventional gaseous sterilization systems typically flow sterilant into the sterilization chamber and exhaust the sterilant to a drain. An open system is described in Picard et al. U.S. Pat. No. 4,435,194. A problem often associated with such open systems is the safe disposal of residual gases. An open flow-through sterilization system that eliminates the problem of residual vapors is described in Cummings et al., U.S. Pat. No. 4,909,999 issued Mar. 20, 1990, entitled "Flow-Through Vapor Phase Sterilization System". One means of providing a closed system is taught by Cummings et al., but that means does not address the problem of moisture build up in the system to be described below.

Several closed systems for steam sterilizers have been developed which recirculate the steam rather than exhausting it. Arrangements for steam autoclaves are disclosed in Linder U.S. Pat. Nos. 3,443,884 and 3,773,466. Another closed steam sterilization system is described in Childers U.S. Pat. No. 4,808,377. In the closed steam sterilization systems, the steam is passed from the sterilization chamber, condensed, passed to a liquid storage compartment and eventually directed to a heater for conversion to steam and reuse in the sterilization chamber.

When the sterilant is steam, moisture in the closed system is not a problem. It is simply recycled for further use in the sterilization process. If other gases were to be used as the sterilant in a closed system, e.g., ethylene oxide, vapor phase hydrogen peroxide or ozone, the buildup of moisture would be highly detrimental to the sterilization process.

When the sterilant of choice is vapor phase hydrogen peroxide, which is typically generated from an aqueous solution of liquid hydrogen peroxide, the natural tendency of hydrogen peroxide vapor to degrade to oxygen and water would exacerbate the problem of moisture buildup in a closed system. The elimination of the need to dispose of residual sterilant vapors, however, commends a closed system for vapor phase hydrogen peroxide sterilization.

An object of the present invention is to provide a closed gaseous sterilization system in which the moisture content of the gases can be controlled. A further object of the present invention is to provide such a system which can be used to sterilize a variety of existing enclosures. Finally, it is an object of the present invention to eliminate problems associated with the disposal of residual sterilant vapors.

SUMMARY OF THE INVENTION

The objects of the present invention are satisfied by the method of decontaminating a sealable enclosure and the contents thereof which includes the steps of sealing the enclosure from fluid communication with atmospheric air and establishing a continuous recirculating flow of a filtered gas, preferably air or nitrogen, through the enclosure and through a means fluidly connected to the enclosure for processing the flow of gas. The processing means is selectively sealed from fluid communication with atmospheric air. The method also includes the steps of reducing the relative humidity of the gas within the flow of recirculating gas to a predetermined level, selectively introducing a vapor decontaminant, preferably vapor phase hydrogen peroxide, into the flow of recirculating gas at a predetermined concentration so that the flow of recirculating gas carries the vapor decontaminant into and through the enclosure and maintaining the continuous flow of recirculating gas and vapor decontaminant through the enclosure for a first predetermined period of time. The first period of time may be that sufficient for sterilizing the enclosure and its contents or may be a period of time sufficient for disinfecting or sanitizing the enclosure and its contents. The relative humidity of the recirculating flow of gas is continuously reduced to about the predetermined level for at least during the first period of time. Following the first period of time, the method further includes the steps of continuing the flow of recirculating gas into and through the enclosure for a second period of time sufficient for removing residual vapor decontaminant from the enclosure. The vapor may be removed by converting the residual vapor decontaminant to a form suitable for disposal. Alternatively, or in addition, the vapor may be removed by physically removing it from the flow of gas.

The method may also include the step of pressurizing the enclosure to a selected elevated level by selectively admitting filtered gas to the processing means or the step of evacuating the enclosure to a selected reduced level by selectively exhausting filtered gas from the processing means.

The relative humidity of the gas is reduced preferably by circulating the flow of gas, or the flow of gas and vapor decontaminant, through a drying agent.

The step of introducing vapor decontaminant into the recirculating flow of gas preferably comprises the steps of passing a liquid decontaminant to a vaporization chamber or some other means for heating the liquid decontaminant to a temperature sufficient for transforming the liquid into vapor and passing the flow of recirculating gas through the vaporization chamber, or heating means, to carry the vapor decontaminant into and through the enclosure. The vapor decontaminant may be introduced into the recirculating flow of gas in continuous increments or in intermittent increments.

Following the second period of time, when the residual vapor decontaminant is removed from the enclosure, water vapor may be optionally introduced into the recirculating flow of gas to humidify the enclosure. When the water vapor is introduced, the circulating flow of gas bypasses the drying agent so that the relative humidity of the gas is not reduced. The step of introducing water vapor into the recirculating flow of gas comprises the steps of passing liquid water to a vaporization chamber or some other means of heating the liquid water to a temperature sufficient for transforming the liquid water to water vapor and passing the recirculating flow of gas through the vaporization chamber, or heating means, to carry the water vapor into and through the enclosure.

The method of the present invention can be practiced in a sealable enclosure which is connected in a sealed relationship to a means for processing a gaseous medium. The processing means is preferably a unit for generating vapor decontaminant and recirculating and controlling the vapor and the humidity of the gaseous medium. The enclosure and the processing means establish a closed circuit for recirculating, decontaminating and controlling the vapor content of a gaseous medium in the enclosure. The means for processing the gaseous medium includes an inlet port connected to an outlet of the enclosure and at least one outlet port connected to corresponding inlets of the enclosure. The processing means includes a circuit proceeding from the inlet of the processing means through a first filter and through a pump for withdrawing the gaseous medium from the enclosure and for pushing the gaseous medium flowing down stream of the pump through a drying agent. The circuit also includes, downstream of the drying agent, at least one and preferably two, means for converting a selected decontaminant into a form suitable for disposal. The circuit proceeds from the converting means to a vaporizer and from the vaporizer to at least one outlet of the processing means. When the outlet port of the processing means is connected to the inlet of the enclosure, the circuit is extended to the enclosure and returns via the outlet of the enclosure to the inlet port of the processing means, when connected, to define the closed circuit.

The processing means also includes at least one liquid reservoir fluidly connected to the vaporizer. An injection pump may be provided to aid in directing the liquid in the reservoir to the vaporizer. At least one liquid reservoir contains a liquid decontaminant, such as an aqueous solution of hydrogen peroxide. A second liquid reservoir, if present, may contain water to humidify the enclosure. First valve means are provided for selectively delivering liquid from the reservoir to at least one heating means.

A second valve means is provided to selectively admit gas through the first filter to the closed circuit to increase the pressure therein. A third valve means and a second filter are provided to selectively exhaust gas through the second filter from the closed circuit to decrease the pressure therein. A fourth valve means and a bypass line are provided to permit the circuit to bypass the drying agent and proceed directly from the pump to the converting means when humidification is desired.

BRIEF DESCRIPTION OF THE DRAWINGS

The present invention can be better understood by reference to the drawings in which.

DETAILED DESCRIPTION OF THE PREFERRED EMBODIMENTS

Figure 1:
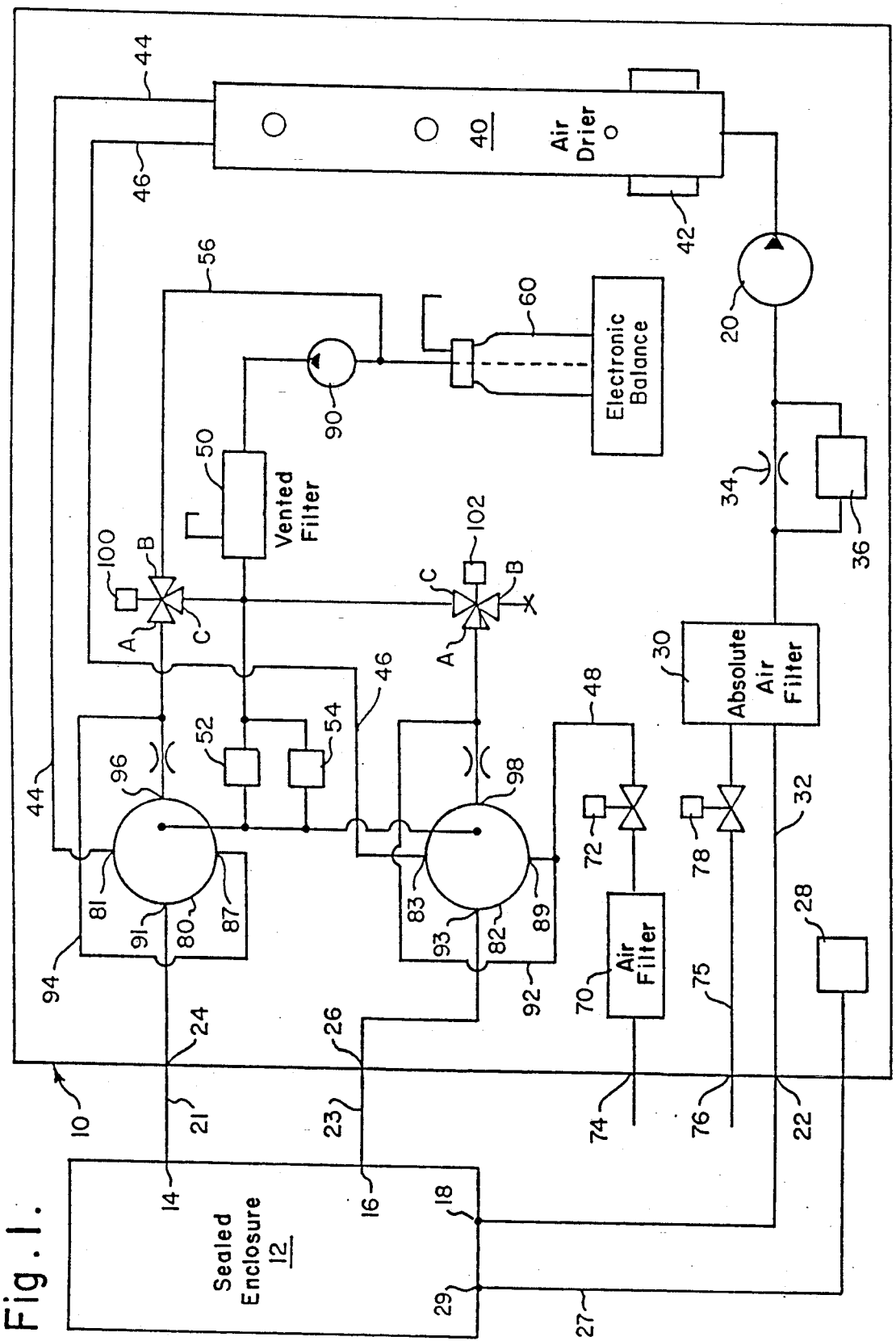
FIG. 1 is a schematic diagram of a preferred embodiment of the recirculation/drying unit of the present invention.
Figure 2:
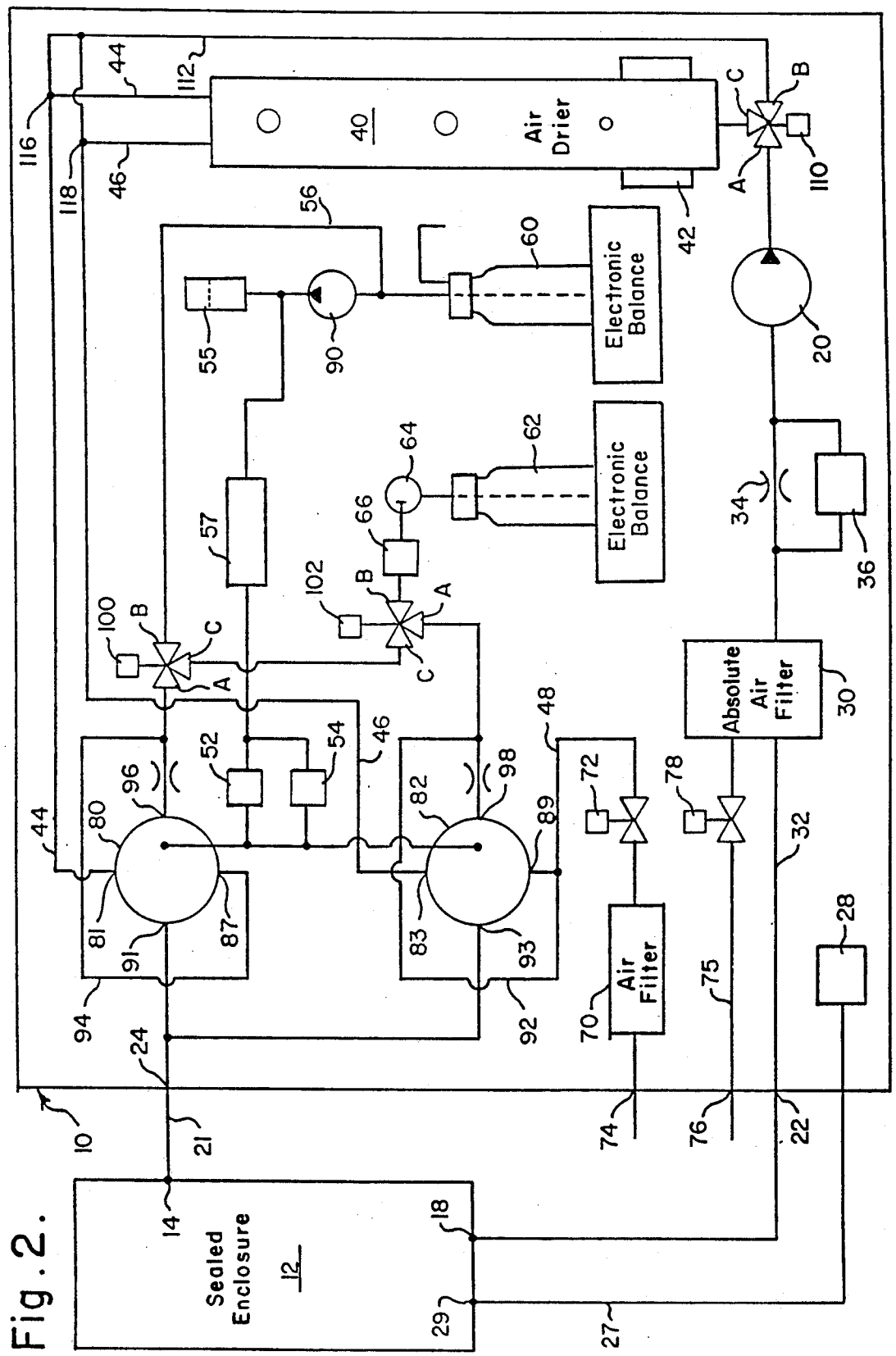
FIG. 2 is a schematic diagram of an alternative embodiment of the recirculation/drying unit of the present invention.

FIGS. 1 and 2 illustrate the preferred embodiments of the recirculation/drying unit 10 of the present invention. The unit 10 is designed for use with almost any sealable enclosure 12. The unit 10 provides a means and a method for decontaminating enclosure 12 and for recirculating, filtering and controlling the water and decontaminant vapor content of the gaseous medium within the enclosure 12 and unit 10. The unit 10 can humidify or dehumidify, introduce decontaminant vapor into or remove it from the gaseous medium of enclosure 12 as the gaseous medium moves through the closed circuit created when unit 10 and enclosure 12 are connected.

The term "decontamination" and variations thereof as used herein shall mean the physical/chemical process (or product) by which an object, contaminated with harmful microbial life, is made safe for handling. The levels of decontamination are sterilization, disinfection and sanitization.

The unit 10 may be a self-contained, detachable unit which can be moved from enclosure to enclosure. Alternatively, the unit 10 may be integrally connected to a single sealable enclosure 12. The sealable enclosure 12 can be an enclosure having rigid walls, such as a clean room, a glove box, fume hood, biological safety cabinet, incubator or refrigerator, or an enclosure having flexible walls, such as a flexible film isolator. The unit 10 can be used regardless of the internal pressure requirements of the enclosure. Unit 10 can be used to decontaminate the interiors and contents of negative pressure enclosures such as those used in virology, positive pressure enclosures, such as clean rooms and enclosures wherein there is no differential in pressure between the interior and the exterior of the enclosure.

Recirculation/drying unit 10 includes generally an air pump 20, a drier 40, a reservoir of liquid decontaminant 60, at least one, but preferably two vaporizer/converters 80 and 82, a fluid injection pump 90 and filters 30, 50 and 70. Valves, sensors and fluid flow lines are also provided.

The decontaminant is preferably vapor phase hydrogen peroxide. Other low temperature chemical decontaminants may be used. For reasons to be explained hereinbelow, steam is not recommended as the decontaminant in the unit 10 of the present invention.

The unit 10 uses air or some other nonhazardous gaseous medium, such as nitrogen, to circulate the decontaminant through the enclosure 12. For purposes of describing the preferred embodiments of the invention and without limiting the invention, the gaseous medium discussed will be air and the decontaminant discussed will be vapor phase hydrogen peroxide. The process discussed will assume that the objective is to sterilize the enclosure 12 and its contents.

Referring to FIG. 1, the enclosure 12 has two inlets, 14 and 16, and an outlet 18. At lease one inlet, 14 or 16 is required. Any suitable know means (not shown), such as a fan, may be provided to create turbulence in the enclosure 12 to mix the vapor sterilant throughout the enclosure. The recirculation/drying unit 10 includes one inlet port 22 and two outlet ports, 24 and 26. At least one outlet port, 24 or 26 is required. Inlets 14 and 16 of enclosure 12 are connected to outlet ports 24 and 26, respectively, of unit 10 by fluid flow lines 21 and 23. Outlet 18 of enclosure 12 is connected to inlet port 22 of unit 10 by fluid flow line 25. By suitable known connections, inlets 14 and 16 and outlet 18 may be releasably or integrally connected in a sealed relationship to their respective fluid flow lines 21, 23 and 25 and outlet ports 24 and 26 and inlet port 22. A pressure sensor 28 located within unit 10 is operatively connected via line 27 to port 29 of enclosure 12 to detect the level of pressure within enclosure 12.

The fluid flow path through unit 10 proceeds through inlet port 22 along return line 32 to an absolute air filter 30, through a flow restricter 34, to pump 20 and to drier 40. A sensor 36 monitors the rate of flow through the flow restricter 34. Pump 20 pulls the air and the vapors within enclosure 12 into unit 10, then pushes the air and vapors through drier 40.

Drier 40 may be any suitable known dessicant column. Molecular sieves known for their selective absorption characteristics may be used in the column. Anhydrous calcium sulfate sold by W. A. Hammand Drierite Company under the name DRIERITE, for example, is a neutral, chemically stable noncorrosive, nondisintegrating, nonpoisonous, regenerative drying agent which is inert to everything except water. The best drying agents are those that react rapidly and irreversibly with water. Some drying agents are soluble in solvents and can be explosive if mishandled. Care should be taken, therefore, to carefully choose a drying agent suitable for the circumstances in which it will be used.

The drier 40 removes water from the gaseous medium as it passes through. Drier 40 is provided with an electric heater 42. The drying agent is regenerated by passing a stream of heated air through it in a suitable known manner, between runs of the recirculation/drying unit 10. Dessicants typically do not work or do not work well at high temperatures. Anhydrous calcium sulfate for example, works well at 75° F., but can work with only some loss of efficiency with a temperature rise up to 200° F. The unit 10, therefore, is not suitable for steam sterilization processes or any other sterilization process wherein the temperature would be greater than the temperature tolerated by the particular drying agent used.

There are two exit paths from drier 40, path 44 and path 46. Path 44 leads to entrance port 81 in vaporizer/converter 80. Air from line 44 passes into port 81 of the converter portion of vaporizer/converter 80. Air from line 46 passes into port 83 of the converter portion of vaporizer/converter 82. Path 46 leads to entrance port 83 in vaporizer/converter 82.

Figure 3:
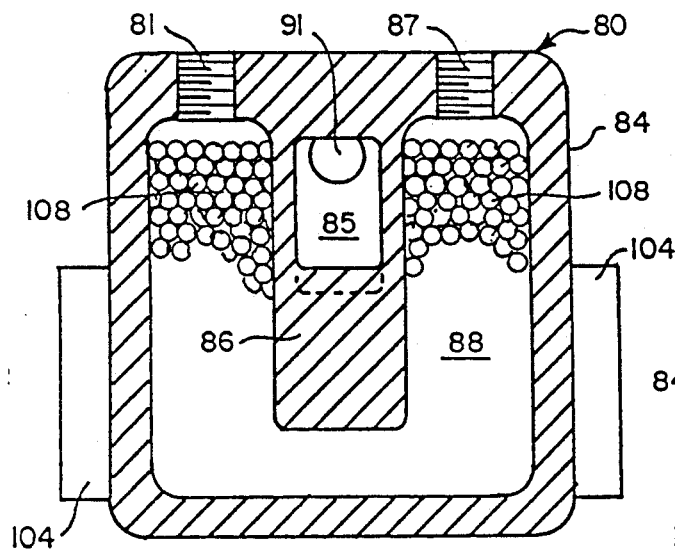
FIG. 3 is a section view of the vaporizer/converter used in the preferred embodiment of the recirculation/-sterilization unit of the present invention.
Figure 4:
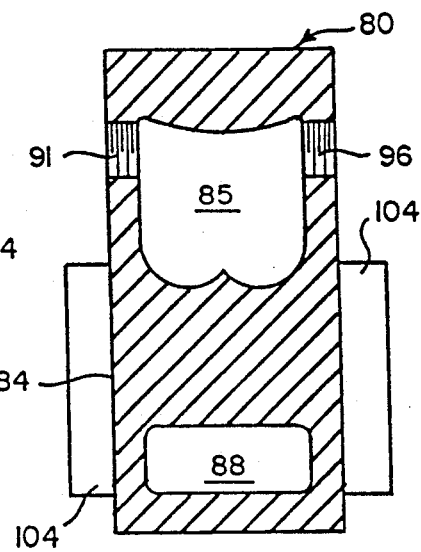
FIG. 4 is a section view of the vaporizer/converter of FIG. 3 along the line III—III.

The vaporizer and converter may be two separate units appropriately connected within unit 10. In the preferred embodiment shown in FIGS. 3 and 4, however, they are used together as a single unit. The vaporizer/converter 80 is described and claimed in U.S. Pat. No. 4,909,999, referenced above, the disclosure of which is hereby incorporated herein by reference. Vaporizer/converter 80 has an external housing 84 and an internal housing 86. An outer chamber 88 is defined therebetween. The internal housing 86 defines an inner chamber 85. The outer chamber 88, which functions as the converter, houses a plurality of spheres 108 which define a low flow-resistant tortuous path having a high surface area for degradation of the sterilant. When the system is used as a hydrogen peroxide sterilization system, the metallic spheres 108 are preferably coated, or made entirely of, copper, platinum, palladium or some other material known to catalytically degrade hydrogen peroxide. A heating element 104, such as an electric band heater, provides temperatures sufficiently high within the outer chamber 88, which, when coupled with the highly catalytic, high surface area tortuous pathway created by spheres 108, nearly instantaneously catalytically decomposes the sterilant vapor. Although the spheres 108 have been demonstrated to work well in decomposing hydrogen peroxide into its degradation products, water and oxygen, any suitable environment which substantially, and preferably completely, converts the sterilant to a form suitable for disposal will suffice.

The previously dried and now heated air exits the converter through port 87 in vaporizer/converter 80 and port 89 in vaporizer/converter 82, and proceeds along lines 94 and 92, respectively through venturi flow restrictors to ports 96 and 98 in the vaporizer portions of vaporizer/converter 80 and 82. Path 92 splits after exiting from port 89 to line 48 which leads to solenoid valve 72, air filter 70 and vacuum bleed-out port 74. Solenoid valve 72 is opened to reduce the pressure within the unit 10 and enclosure 12 when the pressure exceeds a predetermined level. Valve 72 may be opened to reduce pressure by discharging filtered, dried air at timed intervals during a sterilization cycle if the cycle requires a reduction in pressure at a certain stage.

Pressure in unit 10 and enclosure 12 can be increased by opening solenoid valve 78 to admit outside air through port 76 to pressure bleed-in line 75. Air admitted through valve 78 is pulled through air filter 30 by pump 20 and directed to drier 40. The solenoid valve 78 can be opened at predetermined intervals in a sterilization cycle when increased pressure is desirable and can be opened to admit air if the pressure within the unit 10 and enclosure 12 drops below a predetermined desirable level. If the unit 10 is to be used in an explosion proof environment, port 76 can be connected to a slightly pressurized air supply from an external source. The pressurized gas can be used to purge the unit 10 and enclosure 12 before the unit 10 is energized.

At this point, the air can proceed through vaporizer exit ports 91 and 93, unit 10 outlet ports 24 and 26, along lines 21 and 23 and into enclosure 12 through inlets 14 and 16. Enclosure 12 is sealed except for the opening through outlet 18 along line 25 to inlet port 22 of unit 10 and the opening through inlets 14 and 16 to outlet ports 24 and 26 described above. The air may flow through enclosure 12 in a continuous flowing manner. The continuous flow of recirculating air along the closed circuit just described can be used to aerate the enclosure 12 and dehumidify and filter the air by passing all of the air within the system through filter 30, drier 40 and vaporizer/converter 80, 82.

When a sterilization cycle is desired, the recirculating flow of air carries the sterilant vapor from the vaporizer into and through enclosure 12 and returns it to unit 10 along the circuit just described.

Liquid hydrogen peroxide is supplied by reservoir 60. Two three-way valves, 100 and 102, a vented filter 50 or an accumulator 55 and filter 57, an injection pump 90 and pressure switches 52 and 54 are provided. Each three-way valve 100 and 102 has a path A→B or a path C→A. When the path C→A is open in valves 100 and 102, liquid sterilant is drawn from reservoir 60, through injection pump 90 and vented filter 50 where it is split between two lines; one leading to path C→A in valve 100 and one leading to path C→A in valve 102. The liquid sterilant proceeds to ports 96 and 98, of the vaporizer portions of vaporizer/converters 80 and 82, respectively. Pressure switches 52 and 54 control the rate of flow of the sterilant injected into the vaporizers.

Heat from heater 104 and, to some extent, the heat given off during the decomposition of the sterilant, is conducted through the spheres 108 and internal housing 86 to inner chamber 85, which functions as the vaporizer to instantaneously vaporize the liquid sterilant when it enters the inner chamber 85 of vaporizer/converter 80. The vaporizer temperature when used for hydrogen peroxide sterilization is about 60°–150° C. (140°–302° F.). The vapor is then passed through ports 91 and 93 of vaporizer/converters 80 and 82, through outlet ports 24 and 26 of unit 10, along lines 21 and 23 to inlets 14 and 16 and into the enclosure 12. The vapor may pass into the enclosure 12 continually or may pass incrementally as disclosed in Bier U.S. Pat. No. 4,642,165, the relevant portions of which are hereby incorporated herein by reference. The control of the liquid injection is by an electronically controlled pressure compensated flow control that preferably produces a nearly continuous fine mist varying from 0.2 to 18 grams per minute.

The sterilant vapor, as stated above, is carried by the heated flowing air through the sealed enclosure. When the sterilant vapor returns to unit 10 it passes through filter 30 and drier 40. Because the liquid sterilant is an aqueous solution of hydrogen peroxide, a portion of the vapor passed to enclosure 12 is water vapor. The hydrogen peroxide vapors are also degraded to some extent to oxygen and water. The water vapor portion of the degraded sterilant and the water vapor generated from vaporization of the liquid sterilant are substantially absorbed by the drying agent in drier 40. Low humidity air containing some sterilant exits drier 40 along lines 44 and 46 and passes into the converter portions of vaporizer/converters 80 and 82 where any remaining hydrogen peroxide is degraded to oxygen and water. Injection of the sterilant into the vaporizers is continued. The vapor is carried into and through enclosure 12 and returned to unit 10 as described. The sterilization cycle is continued for as long as it takes to sterilize enclosure 12. A shorter period can be used if only disinfection is desired. The flow of sterilant vapor through the flow lines and filters of unit 10 ensures that these components are also sterilized.

When path C→B of three-way divertor valve 100 is opened, the lines containing liquid hydrogen peroxide are directed back to reservoir 60. Since the liquid pump 90 will not permit back flow, this flow path from C→B prevents pressure buildup in the sterilant delivery lines when the hydrogen peroxide breaks down into water and oxygen.

Unit 10 is primarily intended for humidity reduction, sterilization and aeration. However, if humidification is desired, the alternative embodiment illustrated in FIG. 2 can be employed. A water reservoir 62, injection pump 64 and filter 66 are fluidly connected via path B→A through three-way valve 102 to port 98 of vaporizer/converter 82.

A three-way by-pass valve 110 is provided in the line between pump 20 and drier 40. Path A→C of valve 110 directs flow into drier 40 as described above. Path A→B of valve 110 directs the flow of air around drier 40 along path 112 to join paths 44 and 46 at points 116 and 118, respectively.

When humidification is desired, valve 100 is energized C→A but injection pump 90 is not activated. Path B→A of valve 102 is opened and injection pump 64 is activated. Path A→B of valve 110 is opened. Water is drawn from reservoir 62 through injection pump 64 and filter 66, along path B→A of valve 102 to port 98 of the vaporizer portion of vaporizer/converter 82 as well as along path C→A valve 100 to port 96 of vaporizer/converter 80. The water is vaporized in the vaporizer and passed into enclosure 12 through ports 91 and 93, outlet ports 24 and 26, lines 21 and 23 and inlets 14 and 16 along with the flow of air entering the vaporizer from the converter portion of vaporizer/converters 81 and 82.

The moist air is drawn through enclosure 12, exits outlet 18 and proceeds along path 25 to inlet port 22 and return line 32, through filter 30 and pump 20. Pump 20 then pushes the stream of moist air through path A→B of by-pass valve 110, along path 112 to paths 44 and 46 as described. The moist air passes through the converter portions of vaporizer/converters 80 and 82, along lines 94 and 92 to the vaporizer portions of vaporizer/converters 80 and 82 and exits through converter ports 91 and 93 and outlet ports 24 and 26 to inlets 14 and 16 of enclosure 12. That flow pattern is continued until humidification of enclosure 12 is no longer desired.

When aeration alone is desired, valves 100 and 102 are de-energized so that no sterilant and no water can be injected into the vaporizers. Drier 40 removes any moisture or vapor as the air passes through. Residual sterilant vapors are degraded in the converters. When the humidity and sterilant vapor levels have been reduced sufficiently, aeration can be discontinued.

In order to regenerate the circuit, the connections between enclosure 12 and unit 10 at inlets 14 and 16 and outlet 18 are released to create an open circuit. Pump 20 draws in air through filter 30 at a predetermined controlled flow rate and passes it through drier 40. Heater 42 is activated so that this stream of air is heated and thereby removes moisture from the dessicant or molecular sieve material. Suitable known temperature sensors (not shown) in the drier can control regeneration by known means and can determine when regeneration is complete. Any residual sterilant vapor driven off by the regenerating drier 40 is converted to a form suitable for disposal in the converter portions of vaporizer/converters 80 and 82. Moist, warm air exits the outlet ports 24 and 26 to atmosphere.

The recirculation/drying unit 10 of the present invention provides a closed circuit when sealably connected to enclosure 12. It is easier and less expensive to dry the gaseous medium within a room, for example, by means of the closed recirculating circuit of the present invention than to purge the room using a dried gaseous medium. The predried air which results from the present invention will accept more of the preferred sterilant, a 30% by weight aqueous solution of hydrogen peroxide. As the relative humidity of the air within enclosure 12 increases, the amount of vapor phase hydrogen peroxide that can be added without risking over saturation and condensation of the vapor decreases.

Table 1 contains a tabulation of the maximum allowable hydrogen peroxide vapor concentration as a function of the initial relative humidity and temperature, assuming the vaporization of a 30% by weight aqueous solution of hydrogen peroxide. Condensation of the sterilant vapor will not occur when the recommended concentrations in Table 1 are not exceeded.

TABLE I

| Temperature | *Maximum Allowable H₂O₂ Vapor Concentration | | | |
| --- | --- | --- | --- | --- |
| °F. | RH = 0% | RH = 10% | RH = 40% | RH = 80% |
| 50 | 0.750 | 0.626 | 0.325 | 0.081 |
| 59 | 1.061 | 0.889 | 0.467 | 0.117 |
| 68 | 1.481 | 1.241 | 0.661 | 0.166 |
| 77 | 2.043 | 1.720 | 0.913 | 0.224 |

*Assuming vaporization of 30% by weight aqueous solution of $H_2O_2$.

In order to avoid condensation of the sterilant, it is important to reduce the relative humidity in an enclosure prior to introduction of the sterilant vapor. For example, to reduce the relative humidity in a 1000 cubic foot enclosure at 68° F. from 40% to 10%, 151.8 grams of moisture must be removed in a recirculation system. In an open system (i.e., flowing mixer), in order to reduce the relative humidity in the enclosure from 40% to about 6%, three times the amount of air and moisture would have to be flushed through the enclosure. This would require an air drier that is 3 times larger.

Another advantage to a closed recirculating circuit is that less pressure or vacuum is applied to the enclosure as compared to an open circuit. In an open system, a pressure differential must be created which is sufficient to push or pull the gaseous medium through the supply piping, enclosure and exhaust piping. In the recirculating closed circuit, the enclosure acts like "piping" which connects the inlet of a pump to the pumps own outlet. The pressure drop in this piping is negligibly small since the gaseous medium is exiting at the same rate it is entering, and the effective "piping" diameter is the cross-section of the chamber. The pump does not have to be concerned with the absolute pressure of the enclosure because it is pumping "from" and "to" the same pressure. A smaller, less powerful pump can be employed. The recirculating closed circuit of the present invention does not exhaust residual sterilant vapors into the atmosphere. The vapors are returned to the unit 10 from the enclosure 12, dried and decomposed into harmless components which can be recirculated to the enclosure 12 while the system is in operation. Any exhaust to atmosphere during or after the use of the system is through a filter and occurs only after the residual vapors have been decomposed.

A preferred method for employing the recirculation/drying unit 10 of the present invention includes a conditioning phase in which pump 20 is energized to draw the air from enclosure 12 and circulate it through unit 10 to dry and heat it, preferably until the relative humidity of enclosure 12 is reduced to about 10% or less. The air flow rate in the system of the present invention can be from 4-12 SCFM. At that point, valve 100 can be opened to permit liquid sterilant to be metered to the vaporizer portions of vaporizer/converters 80 and 82 as described above. The liquid sterilant is vaporized and carried or drawn with the recirculating air into enclosure 12 as described above. The introduction of vapor phase hydrogen peroxide can be in continuous increments or in intermittent increments at timed intervals depending upon the sterilization cycle to be employed for a particular type of enclosure.

If the sterilization cycle of choice includes evacuation stages or pressurization stages, valves 72 and 78 can be activated to decrease or increase the pressure within enclosure 12. The introduction of sterilant proceeds for a period of time sufficient for sterilizing enclosure 12 and the contents thereof. Alternatively, the introduction can proceed for a period of time sufficient for disinfecting enclosure 12 and it contents. Thereafter, valve 100 is closed and liquid sterilant injection into the vaporizers ceases.

Following the sterilization phase, the recirculation, filtering and drying of the gaseous medium continues in the aeration phase to ensure removal of the sterilant from enclosure 12 and the piping of unit 10. The flow of the gaseous medium through drier 40 and the converters removes any residual sterilant, converting it to a form suitable for disposal. In the case of hydrogen peroxide, the residuals are converted to the harmless degradation products, water and oxygen. When the residuals have been lowered to a desired level, pump 20 can be turned off. Alternatively, a desired positive or negative pressure can be maintained in enclosure 12.

If desired, enclosure 12 can be humidified to return it to the level of relative humidity present prior to the conditioning phase. Pump 20 would remain energized, valve 102 would be opened and pump 64 would be energized to deliver increments of water to the vaporizer. The resulting water vapor is then carried by the flow of air or drawn into enclosure 12. By-pass valve 110 would be activated to divert the flow of moist air away from drier 40 directly to the converters.

Following completion of the conditioning, sterilization, aeration and optional humidification phases, the unit 10 can be disconnected from enclosure 12 to permit regeneration of the drying agent as described above.

Figure 5:
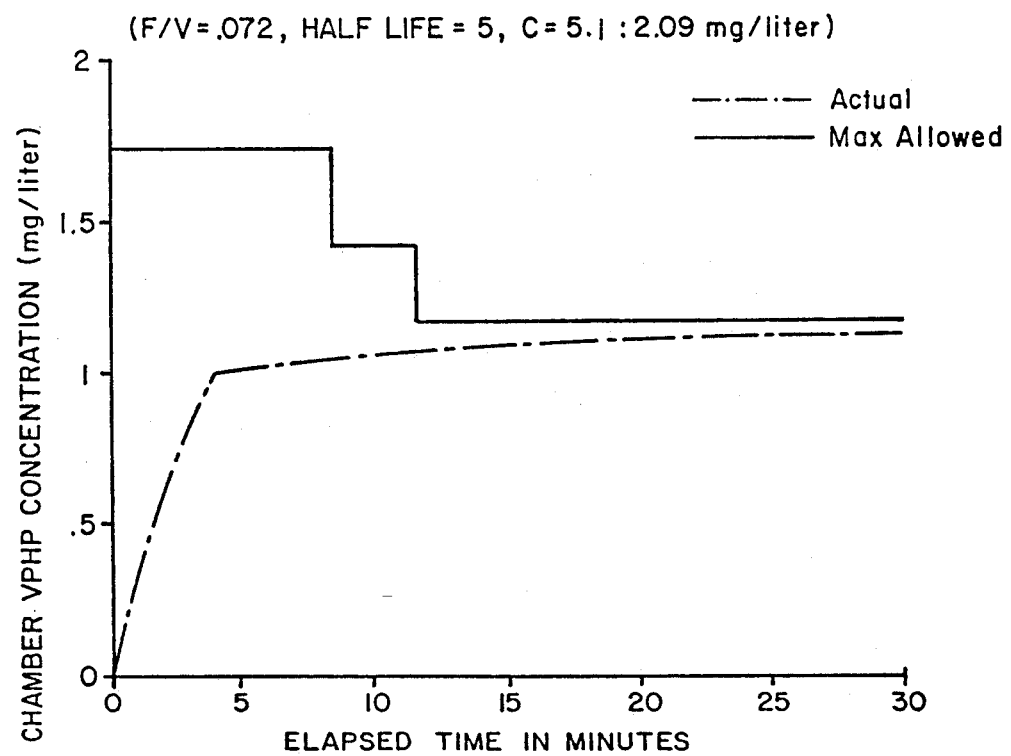
FIG. 5 is a graph showing the theoretical concentration of vapor phase hydrogen peroxide in a 145 cubic foot flexible chamber for a recirculating airflow of 10.5 SCFM.

FIG. 5 illustrates the theoretical concentration of vapor phase hydrogen peroxide in a 145 cubic foot flexible film enclosure. A high injection rate for the first four minutes quickly brings the enclosure up to a concentration of 1 mg/liter. A lower injection rate for the next 26 minutes maintains the sterilant concentration in spite of degradation of the hydrogen peroxide vapor into water and oxygen at the assumed half life of five minutes. The cycle illustrated in FIG. 5 was successfully run under the conditions shown. Biological indicators present in the enclosure demonstrated that sterilization was complete. No condensation of vapors occurred.

Figure 6:
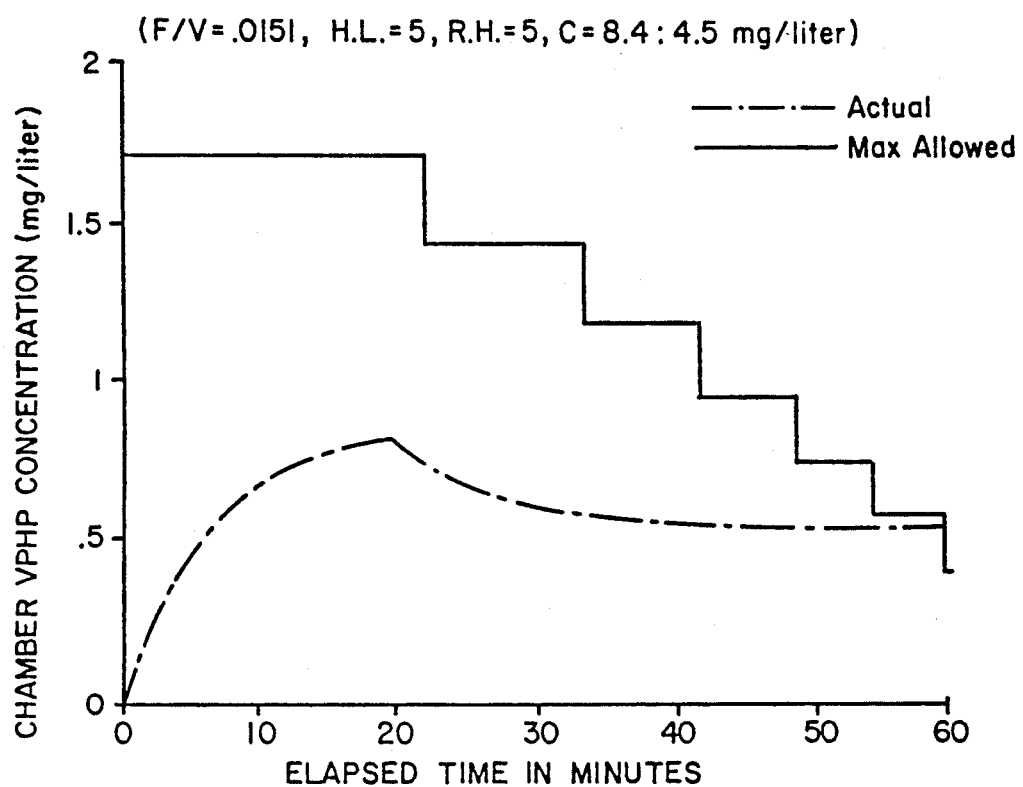
FIGS. 6 and 7 are graphs showing the theoretical concentration of vapor phase hydrogen peroxide having a half-life of ten and five minutes, respectively, in a 728 cubic foot rigid walled room for a recirculating air flow of 11 SCFM.
Figure 7:
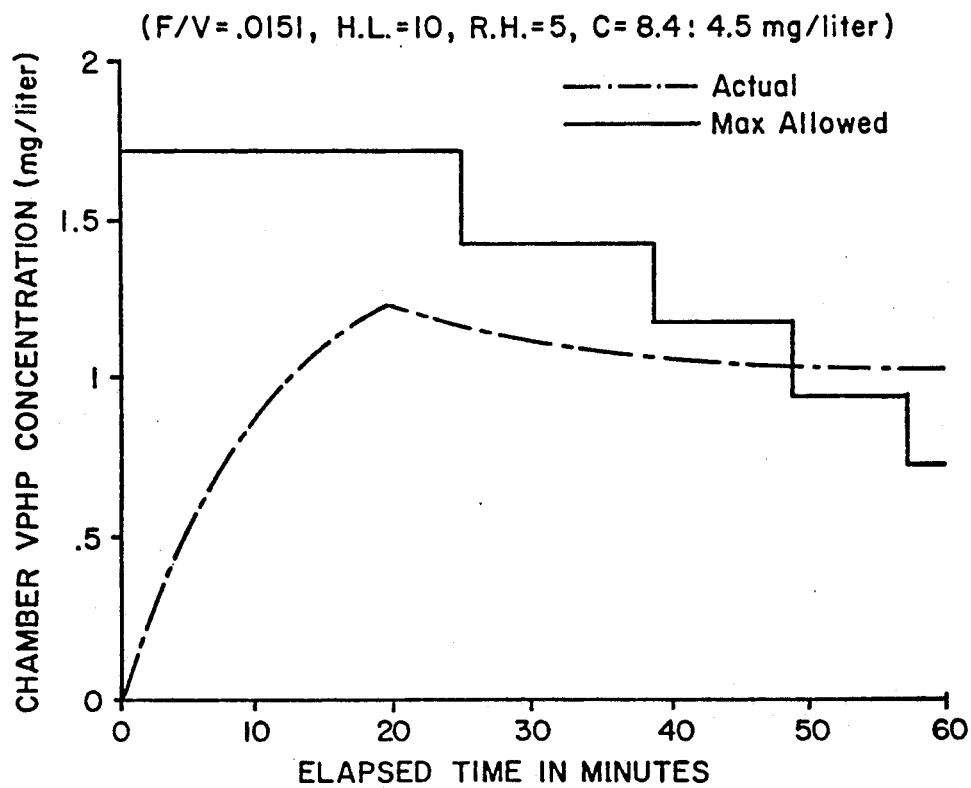

FIGS. 6 and 7 illustrate the theoretical concentration of vapor phase hydrogen peroxide for a 6.5×8.0×14 cubic foot rigid walled room, assuming an air circulation rate of 11 SCFM. The stepped graph above the concentration indicates the maximum allowable vapor phase hydrogen peroxide concentration at the given conditions. If the graphs were to cross, condensation would occur. The initial relative humidity was reduced to less than 10% before the introduction of sterilant vapor.

A theoretical computer generated run was made to determine how long it would take for an enclosure with 10 air exchanges per hour to be reduced from 100% relative humidity to 10% relative humidity in a flowing mixer. It took 97.7 minutes to reduce a 1869 liter enclosure by passing totally dry air through it in a flowing mixer situation.

A run was then made using the same program with different variables to see how it would take to aerate the same enclosure to 1 PPM (1 mg/liter=approximately 720 PPM). It took 220 minutes for the enclosure to go from 3.56 mg/liter (2563 PPM) to 0.0198 mg/liter (14.3 PPM).

During flow through in an open circuit the air has to have 22.778 mg/liter of moisture removed to reduce its relative humidity from 100% to 10% during all phases of the cycle. During the conditioning phase of the method of the present invention, 22.778 mg/liter must be removed from the 1869 liter enclosure. During the sterilization and aeration phases of the method of the present invention, no more than the total amount of sterilant injected must be removed.

A comparison was made of the open and closed circuit methods of the air drying requirements for a 30 minute sterilization cycle on the 1869 liter enclosure with an air flow of 31.15 liter/min. assuming 100% humidity at 80° F.

TABLE II

| Phase of Cycle | Elapsed Time | Moisture Absorbed by Air Dryer | |
|---|---|---|---|
| | | Recirc/Dry Closed Circuit | Flow Through Open Circuit |
| Condition | 97.7 min | 42.6 grams | 69.3 grams |
| Sterilize | 60 min | 30.7 grams | 21.3 grams |
| Aerate | 220 min | | 156.1 grams |
| Total | 337.7 min | 73.3 grams | 246.7 grams |

There is more than a 3:1 difference in the drying requirements of the two systems. The comparison assumed 100% dry air was used to dilute the room during the condition phase of the open circuit flow through method. In reality, only 90% dry air was available. The aeration was ended when 14 PpM moisture remained in the enclosure instead of 1 PPM. It would have further extended the aeration time and increased the drying requirements of the flow through system if the run proceeded until 1 PPM moisture was achieved.

The recirculation/drying unit 10 of the present invention eliminates moisture build up as a problem and thus, is able to maintain the enclosures to be sterilized at higher concentrations of vapor phase hydrogen peroxide for longer periods of time when compared to a recirculating system which does not include drier 40. In such a system, moisture would build up to intolerable levels. Moisture build up is not present in open flow through systems which can exhaust the moist air, but unacceptable amounts of residual sterilant are exhausted with the moist air. The recirculation/drying unit 10 of the present invention has the advantages of the open systems in its ability to maintain sterilant concentration for extended time periods and the advantages of the closed systems in its ability to avoid the introduction of residual sterilant vapors into the atmosphere. Yet, this invention can use a smaller air drier system because the most moisture it ever has to absorb is that initially contained in the gaseous medium within the enclosure plus that injected. A flow through system could have to absorb 3 times that amount of moisture.

What is claimed is:

1. A method of conditioning and decontaminating the interior of a sealable enclosure and the contents thereof comprising:
    providing a sealable enclosure and processing means associated therewith;
    sealing said enclosure from fluid communication with unfiltered atmospheric air;
    filtering a gas and establishing a continuous recirculating flow of said filtered gas through said enclosure and through a means for processing said flow of filtered as fluidly connected to said enclosure and selectively sealed from fluid communication with unfiltered atmospheric air, wherein said processing means comprises a means for drying said flow of filtered gas, a means for heating said flow or filtered gas and conduit means fluidly connecting said drying means to said heating means;
    reducing the relative humidity of said filtered gas to a predetermined level within said recirculating flow of filtered gas by directing said flow and filtered gas through said drying means;
    selectively introducing a vapor decontamination at a predetermined concentration into said flow of recirculating filtered gas after said flow of filtered gas exists said drying means and before said flow of filtered gas enters said enclosure so that said flow of recirculating filtered gas carries said vapor decontaminant into and through said enclosure wherein said vapor is a multicompound vapor and one component is water vapor;
    maintaining said continuous recirculating flow of filtered gas and vapor decontaminant through said enclosure for a first predetermined period of time sufficient for decontaminating said enclosure and any contents therein;
    continuously reducing the relative humidity of said recirculating flow of filtered gas to maintain the relative humidity at about said predetermined level for at least during said first period of time; and
    following said first period of time, discontinuing introduction of vapor decontaminant and continuing said flow of filtered gas into and through said enclosure for a second period of time sufficient for removing residual vapor decontaminant from said enclosure.

2. The method of claim 1 further comprising selectively admitting additional filtered gas to said processing means to increase the pressure within said enclosure to a selected level at a desired time during at least said decontaminating step.

3. The method of claim 1 further comprising selectively exhausting filtered gas from said processing means to reduce the pressure within said enclosure to a selected level at a desired time during at least the decontaminating step.

4. The method of claim 1 wherein the step of introducing a vapor decontaminant into said flow of filtered gas comprises passing a liquid decontaminant to a means for heating said liquid decontaminant to a temperature sufficient for substantially instantaneously transforming said liquid into vapor and passing said flow of filtered gas through said heating means to carry said vapor into and through said enclosure.

5. The method of claim 1 wherein said first predetermined period of time is sufficient for sterilizing said enclosure and said contents.

6. The method of claim 1 wherein said first predetermined period of time is sufficient for disinfecting said enclosure and said contents.

7. The method of claim 1 wherein said first predetermined period of time is sufficient for sanitizing said enclosure and said contents.

8. The method of claim 1 wherein said step of selectively introducing said vapor decontaminant comprises introducing said vapor decontaminant into said flow of filtered gas in successive increments.

9. The method of claim 1 wherein said step of selectively introducing said vapor decontaminant comprises introducing said vapor decontaminant into said flow of filtered gas in intermittent increments.

10. The method of claim 1 further comprising heating said flow of filtered gas before said flow of filtered gas enters said enclosure.

11. The method of claim 1 further comprising creating turbulence in said enclosure to disperse said vapor decontaminant throughout said enclosure.

12. The method of claim 1 further comprising:
following said second period of time, introducing water vapor into said flow of filtered gas to humidify said enclosure; and
discontinuing said step of maintaining the relative humidity of said filtered gas at about said predetermined level.

13. The method of claim 1 wherein said residual vapor decontaminant is removed from said enclosure by converting said residual vapor decontaminant to a form suitable for disposal.

14. The method of claim 1 wherein said residual vapor decontaminant is removed from said enclosure by directing said residual vapor decontaminant out of said enclosure for storage and subsequent disposal.

15. A method for recirculating and controlling the vapor content of a gaseous medium in a sealable enclosure for decontaminating the enclosure and any items therein comprising:
 a. providing a sealable enclosure and sealing said enclosure from communication with unfiltered atmospheric air;
 b. withdrawing gas from said enclosure;
 c. passing such withdrawn gas through a filter;
 d. directing the filtered gas from said filter to a means for removing moisture from the filtered gas;
 e. directing the filtered gas from said moisture removing means to means for degrading a selected sterilant into degradation products suitable for disposal;
 f. directing the filtered gas from said degrading means to means for heating a liquid to a temperature sufficient for transforming liquid in said heating means into a vapor;
 g. directing the filtered gas from said heating means to said enclosure;
 h. repeating steps b. through g. for a first period of time sufficient to reduce the relative humidity of the filtered gas to a predetermined level;
 i. at the end of said first period of time, directing a liquid decontaminant from a liquid decontaminant reservoir to said heating means wherein said liquid decontaminant is transformed into a vapor decontaminant;
 j. continuing the flow of filtered gas through said heating means and introducing said vapor decontaminant into the filtered gas flowing through said heating means and directing the filtered gas and vapor decontaminant from said heating means to said enclosure;
 k. withdrawing the filtered gas and said vapor decontaminant from said enclosure;
 l. passing the filtered gas and said vapor decontamination through said filter;
 m. directing the filtered gas and said vapor decontaminant from said filter to said moisture removing means;
 n. directing the filtered gas and said vapor decontaminant from said moisture removing means to said degrading means wherein said vapor decontaminant is transformed into its degradation products suitable for disposal;
 o. directing the filtered gas and the degradation products from said degrading means to said heating means;
 p. repeating steps i. through o. for a second predetermined period of time sufficient for decontaminating the enclosure and any items therein; and
 q. at the end of said second period of time, discontinuing step i. through j. and continuing steps k. through o. for a third period of time sufficient for removing residual vapor decontaminant from said enclosure and the filtered gas flow and for transforming said residual decontaminant into its degradation products.

16. The method recited in claim 15 further comprising:
 r. at the end of said third period of time, directing water from a water reservoir to said heating means wherein the water is transformed into water vapor;
 s. introducing said water vapor into the filtered gas flowing through said heating means and directing the filtered gas and said water vapor from said heating means to said enclosure;
 t. withdrawing the filtered gas and said water vapor from said enclosure;
 u. passing the filtered gas and said water vapor through said filter;
 v. diverting the filtered gas and the water vapor away from said moisture removing means and directing them to said degrading means;
 w. directing the filtered gas and said water vapor from said degrading means to said heating means; and
 x. repeating steps r. through w. for a fourth period of time sufficient to humidify said enclosure.

17. The method recited in claim 15 further comprising increasing the pressure in said enclosure to a desired elevated level by selectively introducing additional gas through said filter into the flow of filtered gas directed from said filter to said moisture removing means.

18. The method recited in claim 15 further comprising decreasing the pressure in said enclosure to a desired level by selectively exhausting filtered gas through a second filter after passing through said moisture removing means.

* * * * *

UNITED STATES PATENT AND TRADEMARK OFFICE
CERTIFICATE OF CORRECTION

PATENT NO. : 5,173,258

DATED : December 22, 1992

INVENTOR(S) : Robert W. Childers

It is certified that error appears in the above-identified patent and that said Letters Patent is hereby corrected as shown below:

Col. 4, line 62, delete "know" and substitute therefore --known--.

Col. 8, line 13, delete "81" and substitute therefore --80--.

Col. 10, line 1, delete "it" and substitute therefore --its--.

Col. 10, line 61, after "how", add --long--.

Col. 11, line 27, delete "$P_pM$" and substitute therefore --PPM--.

Col. 11, line 64, delete "as" and substitute therefore --gas--.

Col. 12, line 1, delete "or" and substitute therefore --of--.

Col. 12, line 10, delete "exists" and substitute therefore --exits--.

Col. 13, line 34, after "liquid", add --in said heating means--.

UNITED STATES PATENT AND TRADEMARK OFFICE
CERTIFICATE OF CORRECTION

PATENT NO. : 5,173,258

DATED : December 22, 1992

INVENTOR(S) : Robert W. Childers

It is certified that error appears in the above-indentified patent and that said Letters Patent is hereby corrected as shown below:

Col. 13, line 35, delete "in said heating means".

Signed and Sealed this

Second Day of November, 1993

Attest:

BRUCE LEHMAN

Attesting Officer     Commissioner of Patents and Trademarks